US008855776B2

(12) United States Patent
Lin et al.

(10) Patent No.: US 8,855,776 B2
(45) Date of Patent: Oct. 7, 2014

(54) SYSTEM AND METHOD FOR TREATING A NERVE SYMPTOM

(71) Applicant: National Taiwan University, Taipei (TW)

(72) Inventors: Chii-Wann Lin, Taipei (TW); Yeong-Ray Wen, Taichung (TW); Shey-Shi Lu, Taipei (TW); Hung-Wei Chiu, Taipei (TW); Yao Joe Yang, Taipei (TW); Win-Pin Shih, Taipei (TW); Chi-Heng Chang, Taipei (TW); Wei-Tso Lin, Taipei (TW)

(73) Assignee: National Taiwan University (TW)

( * ) Notice: Subject to any disclaimer, the term of this patent is extended or adjusted under 35 U.S.C. 154(b) by 0 days.

(21) Appl. No.: 13/895,523

(22) Filed: May 16, 2013

(65) Prior Publication Data
US 2013/0317564 A1 Nov. 28, 2013

Related U.S. Application Data

(60) Provisional application No. 61/647,974, filed on May 16, 2012.

(51) Int. Cl.
*A61N 1/00* (2006.01)
*A61N 1/36* (2006.01)
*A61N 1/05* (2006.01)

(52) U.S. Cl.
CPC ......... *A61N 1/36014* (2013.01); *A61N 1/36067* (2013.01); *A61N 1/0551* (2013.01); *A61N 1/36064* (2013.01); *A61N 1/3606* (2013.01); *A61N 1/36171* (2013.01); *A61N 1/36153* (2013.01); *A61N 1/36071* (2013.01)
USPC .......................................................... 607/45

(58) Field of Classification Search
CPC ... A61N 1/36; A61N 1/3605; A61N 1/36082; A61N 1/36014
USPC .......................................................... 607/45
See application file for complete search history.

(56) References Cited

U.S. PATENT DOCUMENTS 7,477,945 B2 * 1/2009 Rezai et al. .................... 607/118
7,647,101 B2 * 1/2010 Libbus et al. .................... 607/2

OTHER PUBLICATIONS

Sluijter, M.E., et al., "The effects of pulsed radiofrequency fields applied to the dorsal root ganglion—a preliminary report," The Pain Clinic, vol. 11, No. 2, pp. 109-117, (1998).

* cited by examiner

*Primary Examiner* — George Manuel
(74) *Attorney, Agent, or Firm* — Yang IPCo, PLLC (57) ABSTRACT

An implantable electrical stimulation system for treating a nerve symptom, the system comprising an implantable device. The implantable devices includes a wave generator that is operable to generate a signal wave and a white noise, mix the signal wave and the white noise, and produce an electrical stimulating signal. The system further comprises an electrode unit located in close proximity to a target nerve and is operable to provide the electrical stimulating signal to the nerve. The system further comprises an external controlling device.

11 Claims, 7 Drawing Sheets

SYSTEM AND METHOD FOR TREATING A NERVE SYMPTOM

CROSS-REFERENCE TO RELATED APPLICATION(S)

This application claims priority to U.S. Provisional Patent Application No. 61/647,974, filed on May 16, 2012, the disclosure of which is hereby incorporated by reference in its entirety.

BACKGROUND

1. Field

The present disclosure relates to a system and a method for treating a nerve symptom, and more particularly to an implantable electrical stimulation system and methods for implanting said system.

2. Description of the Related Art

Pulsed radiofrequency, often called radiofrequency lesioning in clinical practice, has been used for over 30 years to treat various pain complications such as cervicogenic headaches, occipital neuralgia, whiplash injury, cervical radicular pain, intercostal neuralgia, lumbar radicular pain, lower back pain, zygapophyseal joints dysfunction, discogenic pain, pain associated with the sacroiliac joint, etc. However, there is little evidence of efficacy after long-term observation of such radiofrequency lesioning treatment in clinical report literatures. This is mainly due to the radiofrequency lesioning treatment principle. According to this principle, the RF cannula is placed near the related nerve tissues of the affected area. The whole RF cannula is coated with insulating material, with only 0.5 to 1 cm of the electrode tip being exposed. Continuous high-frequency electrical stimulation produces high temperatures to burn the nerve tissues, so that the analgesic effect is achieved after the treatment.

When the human body's repair function is activated, the burned nerve tissues will repair themselves. The nerve tissues will not grow back to the original shape, however, but instead will grow randomly on the dead nerve tissues and form a neuroma, which is easy to be pressed and damaged, resulting in the recurrence of pain or even more serious pain.

The output waveform of radiofrequency lesioning is called continuous radiofrequency (CRF). The radiofrequency lesioning temperature can be controlled through the output voltage. The application discloses improvements in methods of continuous radiofrequency (CRF). Previously, a high temperature of up to 80 degrees Celsius was necessary for radiofrequency lesioning to destroy the nervous tissues. Eventually, an experiment using egg whites was used to study the three-dimensional effect of heat lesioning of CRF. An electrode was placed into the egg white for stimulation, and the range of egg white protein deterioration due to the effect of heat from the CRF was observed. Through this research, low-temperature and continuous radiofrequency was developed for effective CRF heat lesioning.

In 1998, Sluijter et al. developed a kind of pulsed radiofrequency (PRF). The analgesic effect can last for up to six months after one stimulation session. The stimulation session uses 500,000 Hz, 45 volt high-voltage RF current with 2 stimulations per second and 20 microseconds per stimulation, which is meant to avoid temperature increases in the stimulation process, so that a cycle includes 20 microseconds of stimulation phase and 480 microseconds of silent phase.

Such PRF can avoid heat lesion of the nerve tissues, and this electrical stimulation treatment has been gradually applied to the dorsal root ganglion (DRG). In animal experiments involving 80 degrees Celsius radiofrequency lesioning for CRF and 42 degrees Celsius for PRF tests on the DRG and sciatic nerve of rats, the rats were killed at different time points for tissue sections. The results showed that the DRG and sciatic nerve of the rats all receiving CRF got irreversible damages, and the nerve tissues showed signs of the phenomenon called Wallerian Degeneration. Only a little bit of edema occurred in the DRG and sciatic nerve of the rats receiving PRF, and the rats returned to normal within a week.

PRF technology has gradually replaced radiofrequency lesioning technology since around 2000, and the clinical reports also show that PRF is safe, reliable, and can replace radiofrequency lesioning technology to treat painful diseases. However, a new treatment method usually takes a very long time to develop in clinical practice, and Evidence Based Medicine needs at least ten years to accumulate sufficient clinical evidences. PRF is still a very new technology; almost just a decade so far. Currently, many people are involved in the research of this technology, and there are more and more related technical documents and clinical evidences, but there is no evidence to prove or distinguish the advantages between PRF and CRF technologies. In addition, the current literature is unclear about the analgesic mechanism of PRF. Sluijter et al. have analyzed the physical properties of PRF: thermal effects are below 42 degrees Celsius, and the magnetic field is approximately equal to the Earth's magnetic field. It is probably that the dense electric field effects affect the nerves mainly responsible for the transmission of pain: C and Aδ nociceptive fibers.

Therefore, there is a need for an improved implantable electrical stimulation system.

SUMMARY

The present disclosure relates to an implantable electrical stimulation system for treating a nerve symptom. An implantable electrical stimulation system may comprise an implantable device and an external controlling device. The implantable device may comprise a wave generator and an electrode unit. A wave generator may be operable to generate a signal wave and a white noise, mix the signal and the white noise, and produce an electrical stimulating signal. An electrode unit may be located in close proximity to a target nerve from providing the electrical stimulating signal to the nerve.

DETAILED DESCRIPTION

The present disclosure comprises an implantable electrical stimulation system operable to reduce the nerve conduction capabilities and inhibit the production of biological molecules in the nerves, in contrast with other traditional high-frequency, high-voltage stimulation methods. A high-frequency implantable electrical stimulation system for treating a nerve symptom by providing radiofrequency stimulation pulses that can be implanted with low-intensity, no-injury, and low-temperature effects is disclosed. The present disclosure also provides a method for treating a nerve symptom, the method comprising providing a radiofrequency stimulation pulses to the target nerve, wherein the radiofrequency stimulation pulse is generated by mixing a signal wave and a white noise.

In an embodiment, the nerve symptom may comprise back pain, chronic pain, motor disorder, dystonia, spasticity, tremor, epilepsy or any pain caused by pressed nerve or damaged nerve.

The implantable electrical stimulation system may comprise an implantable device and an external controlling device. The implantable device may be implanted into a patient having one or more of the nerve symptom(s), and the external controlling device may be used to control, adjust, and/or monitor the parameters and the situations of the electrical stimulation treatment.

The implantable device may comprise at least a wave generator and an electrode unit. The wave generator may be operable to generate a signal wave and a white noise, mix the signal wave and the white noise, and produce an electrical stimulating signal. In an embodiment, the signal wave may be a sine wave, a triangular wave, a square wave, a random wave, or any suitable wave for nerve stimulation, which can be used alone or in combination. In an embodiment, the implantable device comprises one wave generator, which may be operable to generate one or more wave types. In an embodiment, the implantable device comprises more than one wave generator, and each wave generator may be operable to generate one or more wave types.

The electrical stimulating signal may be produced by mixing the signal wave and the white noise, so that the mixed signal wave and the white noise are similar to a natural signal produced by the nervous system. Accordingly, the mixed signal wave and the white noise can provide improved therapeutic effects and reduced side effects.

The electrode unit contained in the implantable device may be a linear type, a circular type, a Swiss-roll type, a clip type, a spring type, or any other type of suitable electrode unit. In an embodiment, the electrode unit comprises multiple electrodes separated by insulating parts. In an embodiment, the electrode unit may be a linear type electrode unit and may comprise two electrodes separated by one insulating part. In an embodiment, the electrode unit may be a circular type electrode unit and may comprise four electrodes separated by four insulating parts.

In an embodiment, the electrode unit may have a width of about 0.5 mm to about 2 mm, and each electrode part may have a length of about 0.5 mm to about 5 mm while the insulating part between the two electrodes may have a length of about 2 mm to about 5 mm. In an embodiment, the electrode unit may have a width of 0.5 mm, 1 mm, 1.5 mm, 2 mm, or any width in between. In an embodiment, each electrode part can have a length of 0.5 mm, 1 mm, 2.5 mm, 3 mm, 4 mm, 5 mm or any length in between, and the insulating part between two or more electrodes can have a length of 2 mm, 3 mm, 4 mm, 5 mm or any length in between.

The electrode unit may be located in close proximity to or surrounding a target nerve for providing the electrical stimulating signal to the nerve. In a specific application, the target nerve may include the nerve tissue of the brain, the spinal cord, and/or the peripheral nerve. In an embodiment, the distance between the electrode unit and the target nerve may be about 2 mm to about 6 mm, and more specifically, may be about 3.5 mm to about 5 mm.

In the present disclosure, the implantable electrical stimulation system further comprises devices for supplying power, controlling, monitoring, or supporting the functions of the system. In an embodiment, the device for supplying power to the implantable electrical stimulation system may comprise a first power supplying unit in the implantable device and a second power supplying unit in the external device. Each of these devices can be added depending on the desired characteristics of the system.

In an embodiment, the implantable electrical stimulation system may further comprise a wireless communication system, which comprises a first wireless communication unit in the implantable device and a second wireless communication unit in the external device. The wireless communication system can transmit the signals or information between the internal, implantable device and the external device. The wireless communication system can be used to charge the implantable device.

In an embodiment, the implantable device may further comprise a sensor for detecting desired parameters such as temperature, impedance, electrophysiological parameters, and the like. The detected parameters may be transmitted by the wireless communication system to the external controlling device. A user or an operator can observe said parameters via a screen or a monitor connected to the external controlling device and make adjustments accordingly.

In an embodiment, the implantable electrical stimulation system can further comprise a micro controlling unit (MCU) system, which comprises a first micro controlling unit in the implantable device and a second micro controlling unit in the external controlling device. Each MCU may be operable to control the electrical stimulation.

In an embodiment, the implantable electrical stimulation system can generate an electrical stimulation with a voltage of about 1V to about 10V, such as 3V, 5V, 8V, 10V or any voltage in between, and a frequency of about 1 KHz to about 1 MKHz such as 100, 200, 500, 700, 100 KHz or any frequency in between.

EXAMPLES

Some specific embodiments of the disclosure may be illustrated by one or more of the examples provided herein.

Example 1

Figure 1:
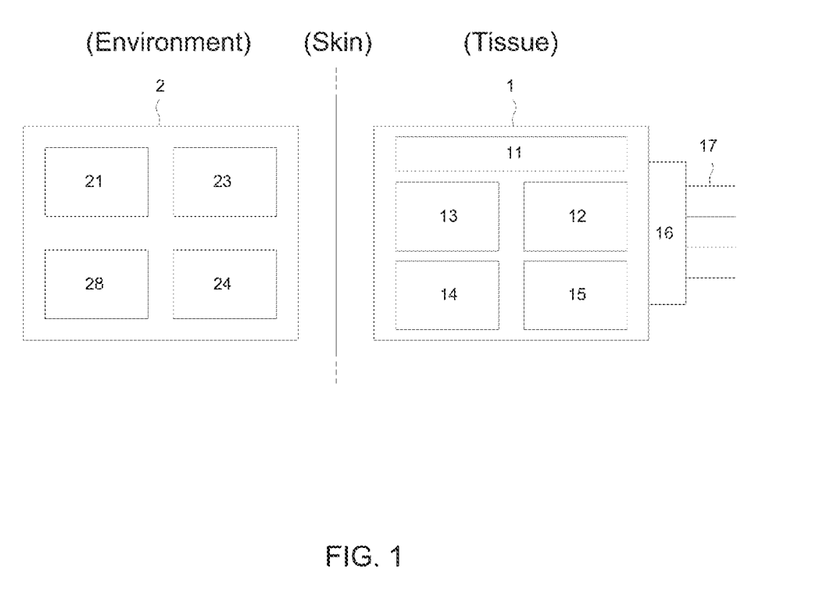
FIG. 1 depicts an embodiment of the implantable electrical stimulation system, in accordance with the present disclosure.
Figure 2:
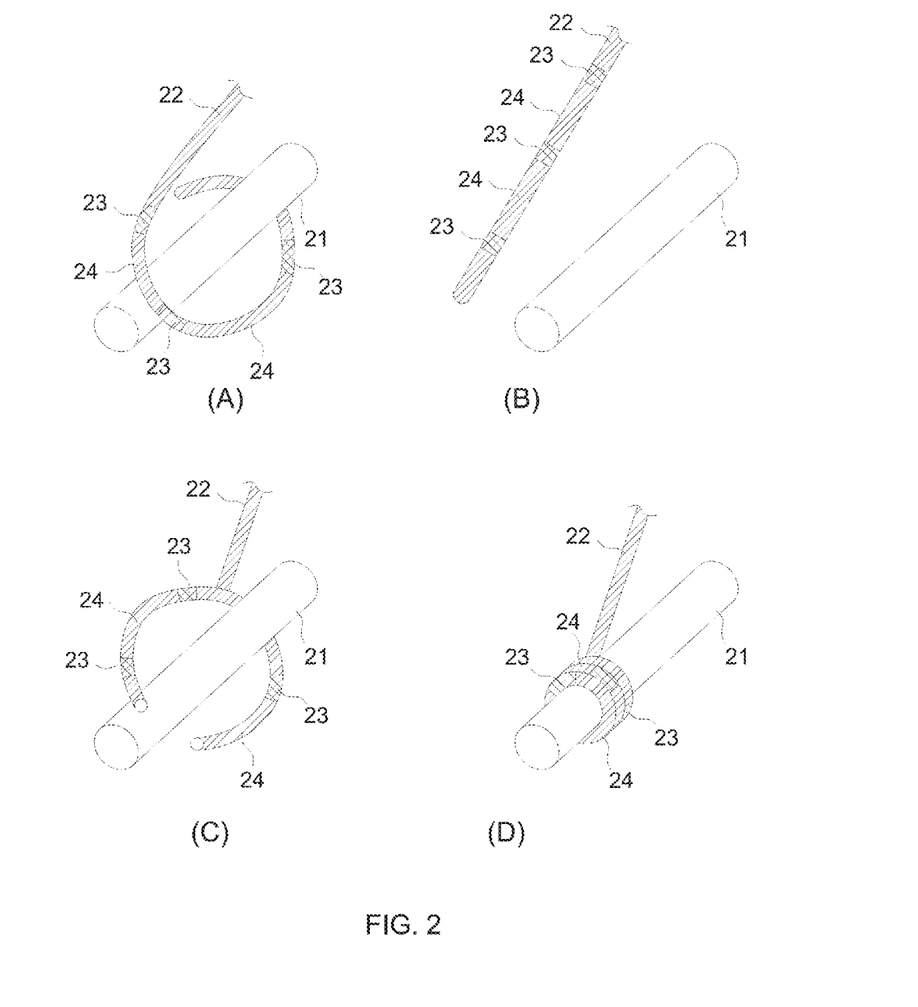
FIGS. 2(A)-(D) depict various embodiments of the electrode of the implantable electrical stimulation system, including (A) linear electrode but placed as Swiss-roll type, (B) linear type electrode, (C) clip-type electrode and (D) spring-type electrode, in accordance with the present disclosure.

FIG. 1 depicts an embodiment of the implantable electrical stimulation system, in accordance with the present disclosure. The implantable electrical stimulation system may comprise an implantable device 1 and an external controlling device 2 separated by a layer of skin. The implantable device 1 may comprise a first micro controlling unit 11, a wave generator 12, a first power supplying unit 13, a first wireless communication unit 14, a sensor 15, a switch 16, and an electrode unit 17. The external controlling device 2 may comprise a second micro controlling unit 21, a second power supplying unit 23, a second wireless communication unit 24, and a screen 28.

FIGS. 2(A)-(D) depict various embodiments of the electrode of the implantable electrical stimulation system suitable for the high-frequency stimulation developed after the simulation optimization. The electrode unit 17 may comprise various types, as shown in FIGS. 2(A)-(D), including (A) a linear electrode located as Swiss-roll type, (B) a linear type electrode, (C) a clip-type electrode, and (D) a spring-type electrode.

Figure 3:
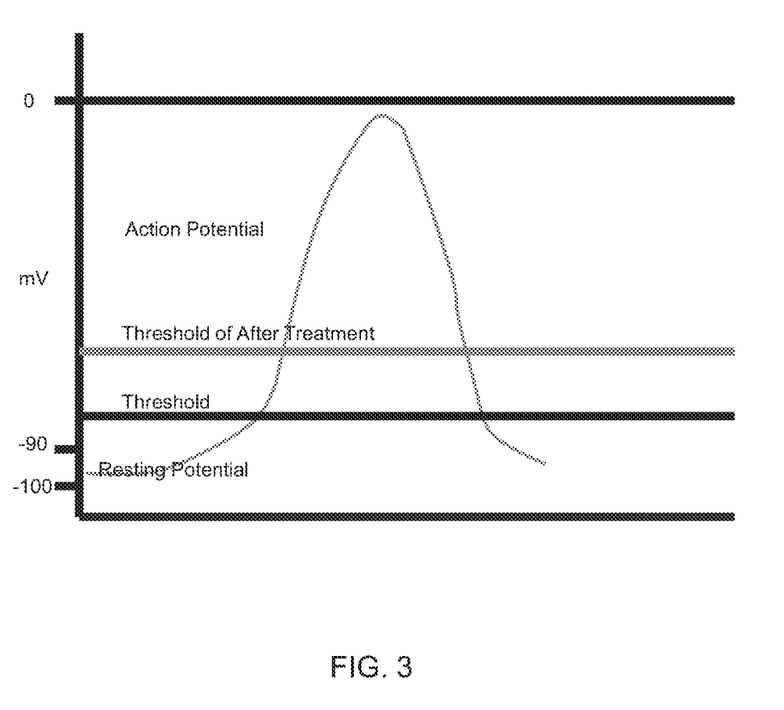
FIG. 3 depicts a nerve threshold line graph, in accordance with the present disclosure.

FIG. 3 depicts a nerve threshold line graph, in accordance with the present disclosure. As shown in FIG. 3, a normal action potential threshold is −70 mV (i.e. the black line), but the threshold may be changed by stimulation such as electrical stimulation. By using the present system, the threshold can be lifted (e.g. the gray line), so that the action potential is difficult to start, and indirectly, excitation of the nerve is difficult to trigger. Accordingly, the pain sensitivity can be reduced and the patient may have relief from pain suffering.

The electrical stimulation can be generated by the present system, more particularly, the electrical stimulation can be generated by the wave generator 12, which is operable to generate a signal wave and a white noise, mix the signal wave and the white noise, and produce an electrical stimulating signal. The electrical stimulating signal generated by mixing the signal wave and the white noise may be similar to natural bio-signal generated by the nervous system.

Figure 4:
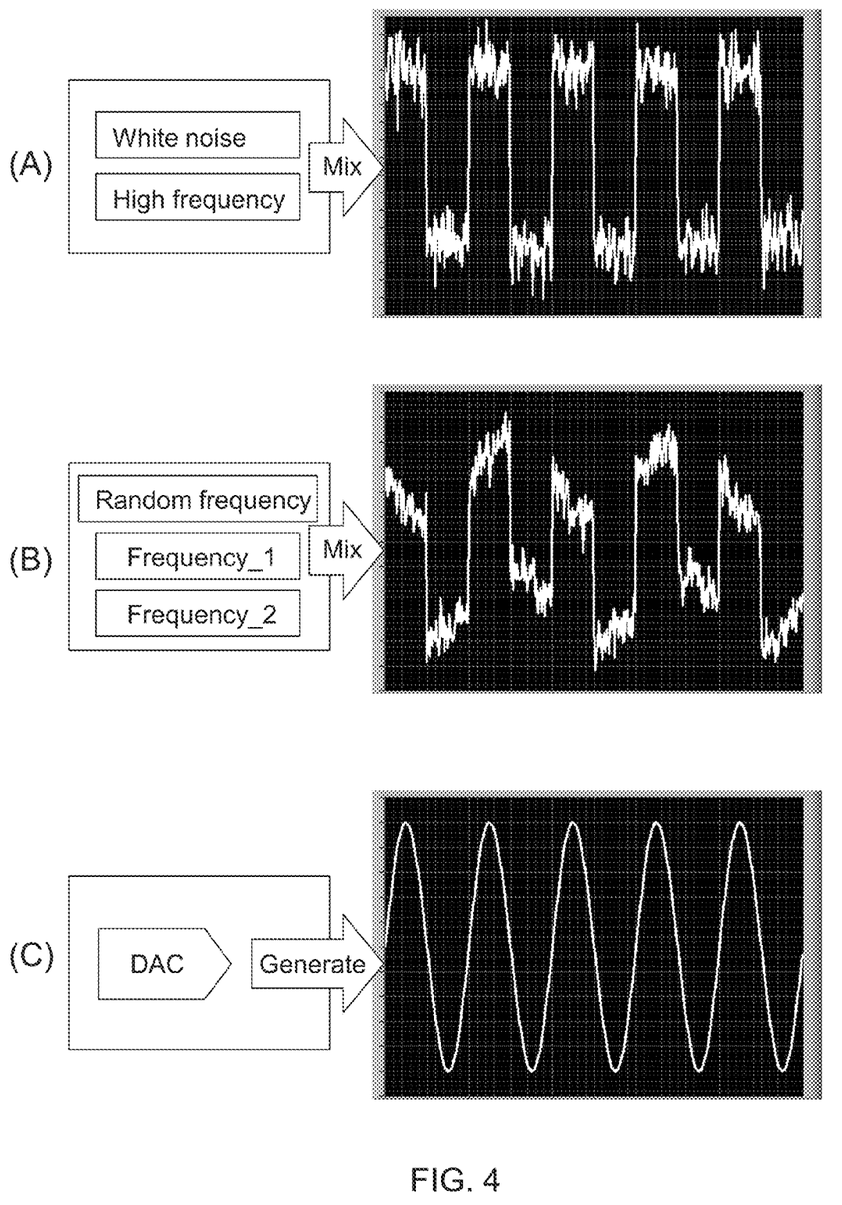
FIGS. 4(A)-(C) depict various embodiments of the electrical signal generated by the present system, in accordance with the present disclosure.

FIGS. 4(A)-(C) depict various embodiments of the electrical signal generated by the present system, in accordance with the present disclosure. As shown in FIGS. 4(A)-(C), the present system is able to generate various electrical stimulations by mixing white noise and regular frequency. The white noise can be a random frequency, as shown in FIG. 4(B). The regular frequency can be a single type or can be multiple types. The operator can decide the type of white noise and the type and the number of the regular frequency wave, depending on the situation of the treatment.

Figure 5A:
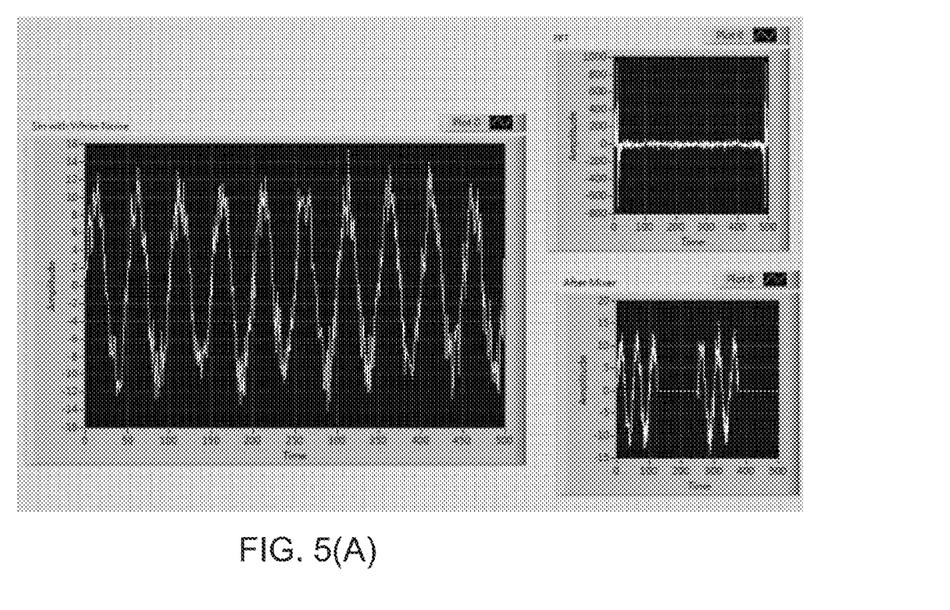
FIGS. 5(A)-(E) depict various embodiments of the electrical signal generated by the present system, in accordance with the present disclosure.

FIGS. 5(A)-(E) depict various embodiments of the electrical signal generated by the present system, in accordance with the present disclosure. In each embodiment, amplitude is measured over a pre-determined period of time. FIG. 5(A) depicts the results of a sine wave mixed with low-intensity white noise, as shown in the left-hand drawing. The top right drawing depicts the Fourier Transform for energy distribution under different frequencies. The bottom right drawing depicts the adjustable stimulation cycle.

Figure 5B:
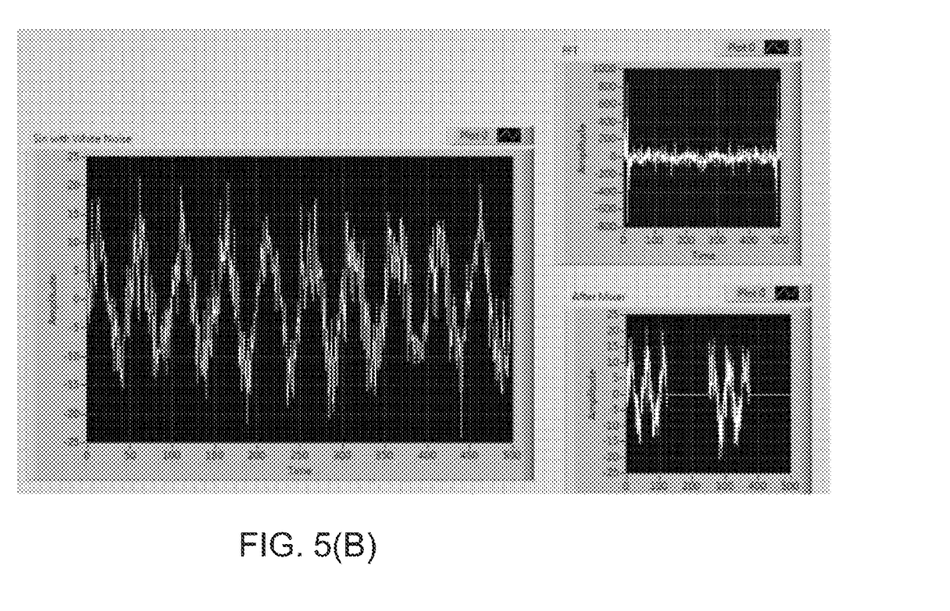

FIG. 5(B) depicts the results of a sine wave mixed with high-intensity white noise, as shown in the left-hand drawing. The top right drawing depicts the Fourier Transform for energy distribution under different frequencies, and it can observe the energy increase of various frequencies. With this method of mixing the sine wave and high-intensity white noise, the energy of various bands can be added for compositional stimulation. In addition, the energy distribution is present from low-frequency to high-frequency, replicating the energy distribution of natural environment. The bottom right drawing depicts the adjustable stimulation cycle.

Figure 5C:
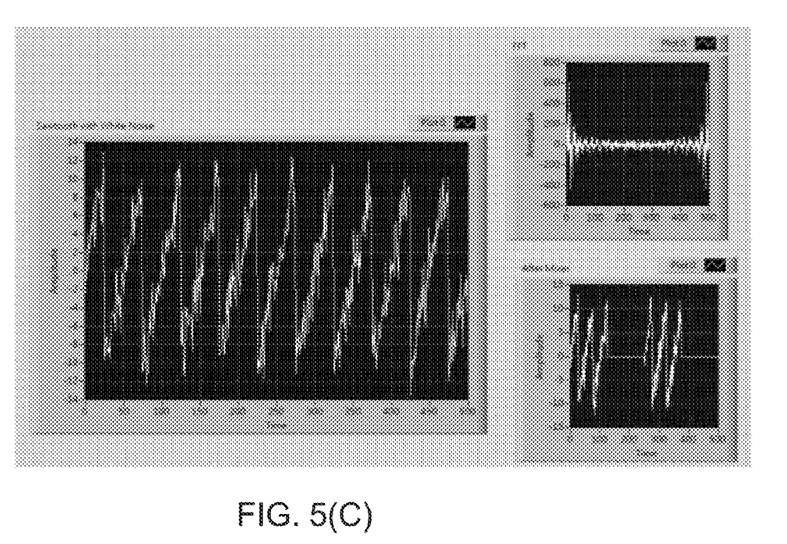

FIG. 5(C) depicts the result of a triangular wave mixed with low-intensity white noise, as shown in the left-hand drawing. The top right drawing depicts the Fourier Transform for energy distribution under different frequencies, and the bottom right drawing depicts the adjustable stimulation cycle.

Figure 5D:
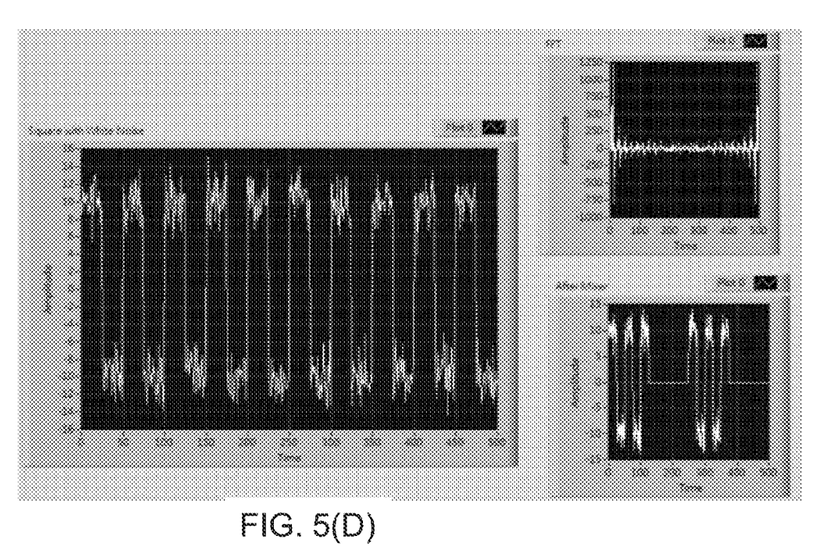

FIG. 5(D) depicts the result of a square wave mixed with low-intensity white noise, as shown in the left-hand drawing. The top right drawing depicts the Fourier Transform for energy distribution under different frequencies, and the bottom right drawing depicts the adjustable stimulation cycle.

Figure 5E:
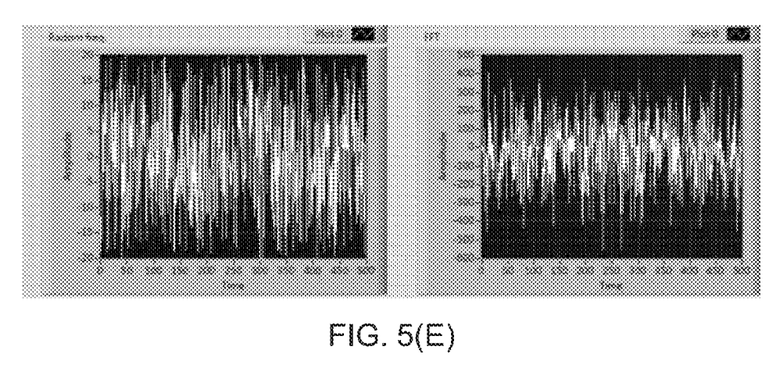

FIG. 5(E) depicts a random stimulation, as shown in the left-hand drawing, and the Fourier Transform for energy distribution under different frequencies, as shown in the right drawing.

As shown in FIG. 1, the external controlling device 2 can provide power to the implantable device 1, and the transmission signal can be passed into the implantable device 1 via one of two ways. In a first way, in the wireless power transmission, signals may be coded and then mixed into the wireless power transmission band. When the relevant unit(s) of the implantable device 1, such as the first power supplying unit 13 and the first wireless communication unit 14, receive power, the internal circuit can decode the signals in the wireless power supply for operation of the MCU 11. In a second way, a wireless transmission module may be used to ensure direct communication between the external controlling device 2 to provide power to the implantable device 1. Preferably, the implantable device 1 has no battery component and directly operates with external power.

According to the above examples of the present disclosure, environmental noise may be added to ensure energy on all frequency spectrums, with more energy in the main band to effectively disturb the nerve and conduct compositional tuning. For example, about 0~1 KHz conventional electrical stimulation mixed with 500 KHz blocking electrical stimulation may provide better treatment results.

Accordingly, the implantable electrical stimulation system disclosed is operable to reduce the nerve conduction capabilities and inhibit the production of biological molecules in nerves. The present system is also different from other traditional high-frequency, high-voltage stimulation. The high-frequency implantable electrical stimulation system that can be implanted with low-intensity, no-injury, and low-temperature effects is developed. While various embodiments in accordance with the principles disclosed herein have been described above, it should be understood that they have been presented by way of example only, and not limitation. Thus, the breadth and scope of this disclosure should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 CFR 1.77 or otherwise to provide organizational cues. These headings shall not limit or characterize the embodiment(s) set out in any claims that may issue from this disclosure. Specifically and by way of example, although the headings refer to a "Technical Field," the claims should not be limited by the language chosen under this heading to describe the so-called field. Further, a description of a technology in the "Background" is not to be construed as an admission that certain technology is prior art to any embodiment(s) in this disclosure. Neither is the "Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

What is claimed is:
1. An implantable electrical stimulation system for treating a nerve symptom, the system comprising:
    an implantable device comprising:
        a wave generator, wherein the wave generator is operable to generate a signal wave and a white noise, mix the signal wave and the white noise, and produce an electrical stimulating signal;

an electrode unit adapted to be located in proximity to a target nerve for providing the electrical stimulating signal to the nerve; and an external controlling device;

wherein the electrode unit comprises more than one electrode separated by insulating parts, and a distance between the electrode unit and the target nerve is between about 2 mm and about 6 mm.

2. The system of claim 1, wherein the system generates radiofrequency stimulation pulses.

3. The system of claim 1, wherein the implantable device further comprises a sensor operable to detect at least one of the group consisting of: temperature, impedance, and electrophysiological parameters.

4. The system of claim 1, wherein the implantable device further comprises a first wireless communication unit operable to transmit signals to the external controlling device.

5. The system of claim 1, wherein the implantable device further comprises a first power supply unit.

6. The system of claim 1, wherein the implantable device further comprises a first micro control unit.

7. The system of claim 1, wherein the external controlling device comprises a second power supply unit, a second wireless communication unit, and a second micro control unit.

8. The system of claim 6, wherein the external controlling device further comprises a screen.

9. The system of claim 1, wherein the signal wave generated by the wave generator is a sine wave, a triangular wave, a square wave, a random wave, or any combination thereof.

10. The system of claim 1, wherein the nerve symptom is selected from a group consisting of: back pain, chronic pain, motor disorders, dystonia, spasticity, tremors, and epilepsy.

11. The system of claim 1, wherein the electrode unit is a linear type, a circular type, a Swiss-roll type, a clip type, and/or spring type electrode unit.

* * * * *